(12) United States Patent
Kim et al.

(10) Patent No.: US 10,195,129 B2
(45) Date of Patent: Feb. 5, 2019

(54) ORAL COMPOSITION FOR TOOTH WHITENING PRODUCT, AND KIT COMPRISING SAME

(71) Applicant: LG HOUSEHOLD & HEALTH CARE LTD., Seoul (KR)

(72) Inventors: Jong-Hoon Kim, Daejeon (KR); Jae-Hyun Ahn, Daejeon (KR); Ji-Hye Kim, Daejeon (KR); In-Ho Lee, Daejeon (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 0 days.

(21) Appl. No.: 15/703,384

(22) Filed: Sep. 13, 2017

(65) Prior Publication Data

US 2018/0000710 A1    Jan. 4, 2018

Related U.S. Application Data

(62) Division of application No. 15/332,229, filed on Oct. 24, 2016, now abandoned, which is a division of application No. 15/037,181, filed as application No. PCT/KR2014/011135 on Nov. 19, 2014, now abandoned.

(30) Foreign Application Priority Data

Nov. 20, 2013 (KR) .................. 10-2013-0141505
Mar. 26, 2014 (KR) .................. 10-2014-0035266

(51) Int. Cl.
| | |
|---|---|
| *A61K 8/02* | (2006.01) |
| *A61K 8/04* | (2006.01) |
| *A61K 8/20* | (2006.01) |
| *A61K 8/22* | (2006.01) |
| *A61K 8/44* | (2006.01) |
| *A61K 8/46* | (2006.01) |
| *A61K 8/63* | (2006.01) |
| *A61K 8/67* | (2006.01) |
| *A61Q 11/00* | (2006.01) |

(52) U.S. Cl.
CPC ............ *A61K 8/466* (2013.01); *A61K 8/0208* (2013.01); *A61K 8/042* (2013.01); *A61K 8/20* (2013.01); *A61K 8/22* (2013.01); *A61K 8/44* (2013.01); *A61K 8/63* (2013.01); *A61K 8/678* (2013.01); *A61Q 11/00* (2013.01); *A61K 2800/592* (2013.01); *A61K 2800/74* (2013.01); *A61K 2800/88* (2013.01); *A61K 2800/884* (2013.01); *A61K 2800/92* (2013.01)

(58) Field of Classification Search
CPC ........................................................ A61K 7/20
USPC ...................................... 424/49, 53; 433/215
See application file for complete search history.

(56) References Cited

U.S. PATENT DOCUMENTS

| | | | |
|---|---|---|---|
| 6,162,055 A | 12/2000 | Montgomery et al. ........ | 433/216 |
| 6,682,721 B2 | 1/2004 | Kim et al. ........................ | 424/53 |
| 6,689,344 B2 | 2/2004 | Chang et al. .................... | 424/53 |
| 6,780,401 B2 | 8/2004 | Kim et al. ........................ | 424/53 |
| 6,946,142 B2 | 9/2005 | Chang et al. .................. | 424/435 |
| 7,601,002 B2 | 10/2009 | Milanovich et al. .......... | 433/215 |
| 2003/0194382 A1* | 10/2003 | Chang .................. | A61K 8/0208 424/53 |
| 2003/0198605 A1 | 10/2003 | Montgomery .................. | 424/53 |
| 2004/0101489 A1 | 5/2004 | Nathoo ........................... | 424/49 |
| 2004/0180008 A1 | 9/2004 | Yamaguchi et al. ............ | 424/53 |
| 2004/0191188 A1* | 9/2004 | Freedman ................ | A61K 8/22 424/53 |
| 2005/0100514 A1 | 5/2005 | Sakaguchi et al. ............. | 424/53 |

FOREIGN PATENT DOCUMENTS

| | | | | |
|---|---|---|---|---|
| JP | 2002-293725 | 10/2002 | ............... | A61K 7/20 |
| JP | 2004-292429 | 10/2004 | ............... | A61K 7/20 |
| KR | 10-2004-0025617 | 3/2004 | ............... | A61K 8/66 |
| KR | 10-2006-0081533 | 7/2006 | ............... | A61K 8/44 |
| KR | 10-0877981 | 1/2009 | ............... | A61K 8/38 |

OTHER PUBLICATIONS

International Search Report (ISR) dated Mar. 3, 2015 in PCT/KR2014/011135 published as WO 2015/076559.
Office Action dated Jun. 15, 2017 in corresponding U.S. Appl. No. 15/332,229.

* cited by examiner

*Primary Examiner* — Walter E Webb
(74) *Attorney, Agent, or Firm* — Harness, Dickey & Pierce, P.L.C.

(57) ABSTRACT

The present invention relates to a composition that acts prior to the action of a tooth whitening composition or tooth whitening patch, the composition containing an oral cavity stimulation alleviating component able to reduce stimulation by the tooth whitening composition or patch. The present invention also relates to a tooth whitening kit whereby oral cavity stimulation is alleviated. The composition that acts prior to the action of a tooth whitening composition or patch of the present invention provides an outstanding tooth whitening effect while alleviating pain by mitigating intra-oral stimulation brought about by the rapid action of a tooth whitening component due to a tooth whitening component active agent.

3 Claims, 4 Drawing Sheets

ORAL COMPOSITION FOR TOOTH WHITENING PRODUCT, AND KIT COMPRISING SAME

CROSS-REFERENCE TO RELATED APPLICATIONS

This application is a divisional application of U.S. application Ser. No. 15/332,229, filed 24 Sep. 2016 which is a divisional application of U.S. application Ser. No. 15/037,181, filed 17 May 2016, which is a national phase application of PCT Application No. PCT/KR2014/011135, filed on 19 Nov. 2014, which claims benefit of Korean Patent Application Nos. KR 10-2014-0035266 filed 26 Mar. 2014 and KR 10-2013-0141505 filed 20 Nov. 2013. The entire disclosures of the applications identified in this paragraph are incorporated herein by references.

FIELD

The present disclosure relates to a composition for mitigating irritation of a tooth whitening product and a kit for tooth whitening including the composition and the tooth whitening product, and more particularly, to and a means for providing a tooth whitening effect with reduced irritation occurring in the mouth suddenly due to a whitening ingredient activator and increased whitening effect.

The present disclosure relates to a composition for enhancing a tooth whitening effect and a kit comprising the same, and more particularly, to a composition for promoting the decomposition of peroxide used as a tooth whitening ingredient to enhance a tooth whitening effect and a kit comprising the same.

BACKGROUND

Recently, with the growing public interest in beauty, people take an increasing interest in tooth whitening. Selections for tooth whitening include toothpastes, mouth rinses, chewing gums, indoor whitening, and tooth whitening solutions using the most common trays available from stores or dentists. A tooth whitening solution generally contains an active ingredient that bleaches the tooth, such as hydrogen peroxide.

Hydrogen peroxide dissolves water, ethanol, and ether well, and as some hydrogen ions dissolute in an aqueous solution, it is a weak acid. Hydrogen peroxide is an unstable material, and activity continues to reduce over time. Thus, general tooth whitening products use a hydrogen peroxide stabilizer that maintains the activity of hydrogen peroxide to prevent the activity reduction of hydrogen peroxide during distribution.

However, when the tooth whitening product is used in real situations, the stabilizer acts as a hindrance factor to activity of hydrogen peroxide, and to solve the problem, a catalyst is used to induce rapid activity of hydrogen peroxide. The catalyst includes a substance that enhances a tooth whitening effect by its reaction with peroxide to generate perhydroxy radicals, and a metal catalyst that promotes the decomposition of peroxide.

On the other hand, when peroxide gets in abrupt touch with the gum, tooth sensitivity and gingival irritation often occurs due to the abrupt action of the whitening ingredient activator for inducing rapid activity of peroxide (e.g., hydrogen peroxide) as mentioned above.

Accordingly, approaches are needed to allow a sufficient tooth whitening effect of peroxide and at the same time, minimize irritation transferred to the tooth and the gum, while maintaining the stability of peroxide during distribution.

DISCLOSURE

Technical Problem

To solve the above problem, the present disclosure is directed to providing a composition for mitigating irritation of a tooth whitening product to reduce the dental and gingival irritation of the tooth whitening product.

Further, the present disclosure is directed to providing a kit for tooth whitening that provides an excellent tooth whitening effect and is less irritating to the gum.

Moreover, the present disclosure is directed to providing a tooth whitening method with an excellent tooth whitening effect and reduced gingival irritation.

The present disclosure is directed to providing a composition for the activation of a tooth whitening ingredient such as hydrogen peroxide.

The present disclosure is further directed to providing a composition for further improvements to the effect of a tooth whitening ingredient, wherein the composition is used with a composition or patch for tooth whitening.

The present disclosure is further directed to providing a composition for enhancing a whitening effect in which the whitening effect of a tooth whitening ingredient can be further promoted by the best catalyst effect.

Technical Solution

To achieve the above objects, the present disclosure provides a kit for tooth whitening containing an oral irritation mitigating ingredient, preferably a kit for tooth whitening with an excellent tooth whitening effect while mitigating gingival irritation caused by the activation of a tooth whitening ingredient, in particular, peroxide.

The kit for tooth whitening according to the present disclosure includes an oral irritation mitigating ingredient, preferably a first agent containing an oral irritation mitigating ingredient and a tooth whitening ingredient activator; and a second agent containing a tooth whitening ingredient.

The oral irritation as used herein includes all types of irritation phenomena including swelling, redness, and pain occurring on the tooth and the gum due to the activation of a tooth whitening ingredient, in particular, peroxide.

The mitigation refers to reduction or relief of oral irritation such as above, and is understood as a broad concept including alleviation, prevention, and treatment.

The tooth whitening ingredient according to the present disclosure may include at least one selected from hydrogen peroxide, carbamide peroxide, calcium peroxide, tetrasodium pyrophosphate peroxidate, sodium bicarbonate, and a chloride-based bleaching agent, preferably at least one selected from the group consisting of hydrogen peroxide, carbamide peroxide, calcium peroxide, and tetrasodium pyrophosphate peroxidate, and more preferably may include hydrogen peroxide or carbamide peroxide.

The tooth whitening ingredient may be present in an amount of 0.01 wt % to 50 wt %, preferably 1 wt % to 30 wt %, and most preferably 2.5 wt % to 20 wt %, per the total weight of the second agent.

Further, the tooth whitening ingredients may be mixed with a stabilizer to prevent the activity reduction during distribution.

The stabilizer may include at least one selected from the group consisting of sodium pyrophosphate, sodium acid pyrophosphate, sodium metaphosphate, sodium polyphosphate, sodium potassium pyrophosphate, potassium pyrophosphate, ultrametaphosphate, sodium acid polyphosphate, ethylenediaminetetraacetate, aminotrimethylenephosphate and its salt, hydroxyethylenediphosphonate and its salt, ethylenediaminetetramethylenephosphonate and its salt, diethylenetriaminepentamethylenephosphonate and its salt, alkyl aryl sulfonate, an alkyl sulfonate salt, an alkyl carboxylate salt, alkyl diphenyl oxide disulfonate, Span 20 (Sorbitan Monolaurate), Span 40 (Sorbitan Monopalmitate), Span 60 (Sorbitan Mono stearate), Span 80 (Sorbitan Monooleate), Span 85 (Sorbitan Trioleate), Tween (POE sorbitan fatty acid ester) family and mixtures thereof.

The tooth whitening ingredient activator may promote the activity of a tooth whitening ingredient, and may be used to prevent the hindrance of whitening activity on the tooth by the stabilizer used for stabilization of the whitening ingredient during distribution of products and to induce an excellent whitening effect.

The tooth whitening ingredient activator may include, but is not limited to, substances for activation of peroxide generally used in the art. However, the tooth whitening ingredient activator may preferably include a divalent or trivalent metal catalyst, a pH adjuster or mixtures thereof.

The divalent or trivalent metal catalyst may promote the decomposition of peroxide. The divalent or trivalent metal catalyst may preferably release calcium, magnesium, manganese, copper, iron or potassium ion, and more preferably, magnesium chloride, magnesium gluconate, ferrous lactate, ferrous gluconate, iron chloride, manganese sulfate, manganese gluconate, manganese chloride and manganese citrate are available.

The pH adjuster reacts with peroxide to generate perhydroxy radicals, thereby enhancing the tooth whitening effect, and an alkali pH adjuster may include, but is not limited thereto, at least one selected from the group consisting of sodium hydroxide, potassium hydroxide, sodium phosphate, disodium phosphate, trisodium phosphate, sodium pyrophosphate, sodium citrate, and EDTA-4Na. The alkali pH adjuster may be present in an optimum amount such that the pH of the composition is 8~11.

In using the tooth whitening product including the tooth whitening ingredients, the stabilizer acts as a hindrance factor to activity of the whitening ingredient, and to solve the problem, the above mentioned tooth whitening ingredient activator is used. In this instance, sudden activation of the whitening ingredient causes an irritating sensation in the mouth, and particularly, causes gingival irritation and damage.

In the kit of the present disclosure, the first agent may include at least one oral irritation mitigating ingredient selected from the group consisting of amino acids including methionine, cysteine and taurine; organic acids including ursodeoxycholic acid and tauroursodeoxycholic acid; and vitamins including vitamins A, C and E, preferably amino acids including methionine, cysteine and taurine, and more preferably taurine, for the purpose of excellent whitening action with mitigated irritation in the mouth such as above.

The oral irritation mitigating ingredient may be included in either the first agent or the second agent or both of the first agent and the second agent, but preferably may be included in the first agent.

It is thought that the irritation mitigating effect will be highest when applying and the second agent containing the tooth whitening ingredient after applying the oral irritation mitigating ingredient to the tooth surface together with the whitening ingredient activator.

The oral irritation mitigating ingredient according to the present disclosure may be present in an amount of 0.001 to 10 wt %, preferably 0.01 to 5 wt %, and more preferably 0.05 to 3 wt %, per the total weight of the first agent.

When the amount of the oral irritation mitigating ingredient is less than 0.001 wt %, it is difficult to expect an optimum effect on irritation mitigation, and when the amount is more than 10 wt %, the whitening effect of hydrogen peroxide may be affected, and consequently, the overall whitening effect of the present disclosure may reduce.

The first agent included in the kit for tooth whitening of the present disclosure is preferably in gel state that can be attached to the tooth by its viscosity, but may be used in dry state.

Here, available polymers may be selected from poly alkyl vinyl ether-maleic acid copolymer (PVM/MA copolymer, Gantrez AN 119, AN 139, S-97), poly vinyl alcohol, poly acrylic acid, Poloxamer (poly(ethylene oxide)-poly(propylene oxide)-poly(ethylene oxide) triblock copolymer), poly ethylene oxide (Polyox), poly vinyl pyrrolidone-vinyl acetate copolymer (PVP/VA copolymer; Luviskol VA, Plasdone S PVP/VA), poly vinyl pyrrolidone (PVP, K15~K-120), Polyquaterium-11 (Gafquat 755N), Polyquaterium-39 (Merquat plus 3330), carboxy poly methylene (Carbopol), hydroxy propyl methyl cellulose, hydroxy ethyl cellulose, hydroxy propyl cellulose, gelatin, sodium alginate or mixtures thereof. Their solvent may primarily include either water or ethanol, or mixtures thereof, and other organic solvents may include, for example, ethyl acetate, methylene chloride, isopropyl alcohol and acetonitrile, alone or in combination at a controlled ratio.

The second agent contains the tooth whitening ingredient, and may maintain the shape of the product and protect the active ingredients. The second agent of the present disclosure may be produced in the form of a patch that can be attached to the tooth surface. Preferably, the first agent may be in gel formulation, and the second agent may be in patch form. The patch that is attached to the tooth according to the present disclosure may be produced by, for example, the methods disclosed in U.S. Pat. Nos. 6,682,721, 6,689,344, 6,780,401, and 6,946,142, but the present disclosure is not limited to the ingredients and producing method of the patch.

According to other embodiments of the present disclosure, the present disclosure provides a composition for mitigating oral irritation of a tooth whitening product including, as an active ingredient for mitigating oral irritation of the tooth whitening product, amino acids including methionine, cysteine and taurine; organic acids including ursodeoxycholic acid and tauroursodeoxycholic acid; and vitamins including vitamins A, C and E.

The composition may further include a tooth whitening ingredient activator.

The composition for mitigating oral irritation is used before the application of the tooth whitening product, and this is to reduce irritation in the mouth or relieve the pain caused by the sudden activation of the tooth whitening ingredient by the tooth whitening ingredient activator.

The oral irritation mitigating ingredient may be present in an amount of 0.01 to 10 wt %, preferably 0.1 to 5 wt %, and more preferably 0.15 to 3 wt %, per the total weight of the composition.

To achieve the above objects, the present disclosure provides a pretreatment composition for enhancing a tooth whitening effect of a composition or patch for tooth whitening containing peroxide, wherein the pretreatment composition includes a metal salt catalyst for releasing a trivalent metal ion in an aqueous solution, and is applied to the tooth surface before the use of the composition or patch for tooth whitening.

Peroxide primarily used as the tooth whitening ingredient needs to be stabilized during distribution and immediately activated at the time of use, in order to enhance the whitening effect.

Accordingly, for immediate activation of the tooth whitening ingredient such as hydrogen peroxide, a method has been proposed in which a catalyst is first applied to the tooth in liquid or gel formulation for pretreatment of tooth whitening, and subsequently, a patch for whitening is used thereon.

The present disclosure increases a metal salt catalyst that serves as an activator to increase the activity of the tooth whitening ingredient.

The metal salt catalyst may promote the activity of the tooth whitening ingredient, and may be used to prevent the hindrance of whitening activity on the tooth by the stabilizer used for stabilization of the whitening ingredient during distribution of the product and to induce an excellent whitening effect.

The inventors found an unexpected effect that a tooth whitening effect of a tooth whitening composition or patch dramatically increased when pretreatment was carried out using a trivalent metal ion during various experiments related to the tooth whitening composition or patch, and particularly that iron chloride ($FeCl_3$) showed a remarkably superior effect than other metal ions.

The iron chloride shows a particularly excellent tooth whitening effect, and besides, may favorably contribute to the preparation of gel formulation due to excellent hygroscopic properties.

The composition containing the iron chloride may be applied to the tooth surface before the use of the composition or patch for tooth whitening.

The iron chloride may be present in an amount of 0.01 to 5 wt %, preferably 0.1 to 3 wt %, and more preferably 0.3 to 1 wt %, per the total weight of the composition.

When the amount of the iron chloride is less than 0.01 wt %, the effect on the promotion of peroxide decomposition may be insufficient, and when the amount is more than 5 wt %, the problem with an irritating sensation on the tooth and in the mouth may occur.

The pretreatment composition may have a property that allows for attachment to the tooth surface to prevent the tooth whitening composition or patch from flowing down when the tooth whitening composition or patch is applied to the tooth, and to improve the attachment to the tooth, may be preferably in gel formulation.

The gel formulation as used herein includes liquid formulation having viscosity, and is used, in broad sense, to include a less flowable state than liquid formulation.

To be formulated as gel, the pretreatment composition may further include a water soluble polymer and a solvent, and may further include substances such as an abrasive and an emulsifier.

Available polymers which play a role in the adhesion to the tooth may be selected from poly alkyl vinyl ether-maleic acid copolymer (PVM/MA copolymer, Gantrez AN 119, AN 139, S-97), poly vinyl alcohol, poly acrylic acid, Poloxamer (poly(ethylene oxide)-poly(propylene oxide)-poly(ethylene oxide) triblock copolymer), poly ethylene oxide (Polyox), poly vinyl pyrrolidone-vinyl acetate copolymer (PVP/VA copolymer; Luviskol VA, Plasdone S PVP/VA), poly vinyl pyrrolidone (PVP, K15~K-120), Polyquaterium-11 (Gafquat 755N), Polyquaterium-39 (Merquat plus 3330), carboxy poly methylene (Carbopol), hydroxy propyl methyl cellulose, hydroxy ethyl cellulose, hydroxy propyl cellulose, gelatin, sodium alginate or mixtures thereof. Their solvent may primarily include either water or ethanol, or mixtures thereof, and other organic solvents may include, for example, ethyl acetate, methylene chloride, isopropyl alcohol and acetonitrile, alone or in combination at a controlled ratio.

The abrasive may include any one selected from precipitated silica, silica gel, zirconium silicate, calcium hydrogenphosphate, calcium hydrogenphosphate dihydrate, hydrous alumina, light calcium carbonate, heavy calcium carbonate, calcium pyrophosphate, insoluble metaphosphate, aluminum silicate, or mixtures thereof.

According to another embodiment of the present disclosure, the present disclosure provides a kit for tooth whitening, including (a) a composition including a metal salt catalyst to release a trivalent metal ion in an aqueous solution state; and (b) a composition or patch for tooth whitening containing peroxide wherein the composition or patch for tooth whitening comes into contact with said composition.

According to still another embodiment of the present disclosure, the kit may further include a means for applying to the tooth surface to attach the composition in gel formulation to the tooth surface, and preferably may be in the form of a brush and a sponge.

The patch for tooth whitening may be produced in the form of a patch that can be attached to the tooth surface, and the patch that is attached to the tooth according to the present disclosure may be produced by the methods disclosed in, for example, U.S. Pat. Nos. 6,682,721, 6,689,344, 6,780,401, and 6,946,142, but the present disclosure is not limited to the ingredients and producing method of the patch.

The peroxide may include at least one selected from the group consisting of hydrogen peroxide, carbamide peroxide, calcium peroxide, sodium percarbonate, sodium perborate, and tetrasodium pyrophosphate peroxidate, and more preferably, hydrogen peroxide or carbamide peroxide.

The tooth whitening ingredient may be present in an amount of 0.01 wt % to 50 wt %, preferably 0.1 wt % to 30 wt %, and most preferably 0.5 wt % to 20 wt %, per the total weight of the patch.

The tooth whitening ingredient may be mixed with a stabilizer.

The stabilizer may include at least one selected from the group consisting of sodium pyrophosphate, sodium acid pyrophosphate, sodium metaphosphate, sodium polyphosphate, sodium potassium pyrophosphate, potassium pyrophosphate, ultrametaphosphate, sodium acid polyphosphate, ethylenediaminetetraacetate, aminotrimethylenehosphate and its salt, hydroxyethylenediphosphonate and its salt, ethylenediaminetetramethylenephosphonate and its salt, diethylenetriaminepentamethylenephosphonate and its salt, alkyl aryl sulfonate, an alkyl sulfonate salt, an alkyl carboxylate salt, alkyl diphenyl oxide disulfonate, Span 20 (Sorbitan Monolaurate), Span 40 (Sorbitan Monopalmitate), Span 60 (Sorbitan Mono stearate), Span 80 (Sorbitan Monooleate), Span 85 (Sorbitan Trioleate), Tween (POE sorbitan fatty acid ester) family and mixtures thereof.

To allow soft bending along the curved surface of the tooth, the patch may include a plasticizer such as polypropylene glycol, glycerin or polyethylene glycol, castor oil and hydrogenated castor oil.

Advantageous Effects

The present disclosure provides a composition for mitigating irritation of a tooth whitening product to mitigate irritation in the mouth that may occur when a tooth whitening ingredient is used alone or in conjunction with a tooth whitening ingredient activator, and a kit for tooth whitening including the composition and the tooth whitening product.

The composition for mitigating irritation and the tooth whitening product according to the present disclosure may provide an excellent tooth whitening effect and minimize irritation in the mouth, in particular, gingival irritation.

The composition for enhancing the tooth whitening effect of the composition or patch for tooth whitening containing peroxide according to the present disclosure may further improve the tooth whitening effect of the composition or patch including the tooth whitening ingredient.

In addition, the composition of the present disclosure allows the composition or patch for tooth whitening to exhibit the whitening effect in a short time.

BEST MODE

Hereinafter, the present disclosure will be described in detail through the following embodiments. However, the embodiments according to the present disclosure may be modified in many different forms, and the scope of the present disclosure shall not be construed as being limited to the embodiments mentioned below. The embodiments of the present disclosure are provided for illustration to help a full understanding of the present disclosure.

Examples 1-4 and Comparative Examples 1-2

A tooth whitening kit according to the present disclosure was produced by a general method in the art according to the ingredient ratios as shown in the following Table 1. The amount unit in the following Table 1 is wt %.

TABLE 1

| | Comparative example 1 | Comparative example 2 | Example 1 | Example 2 | Example 3 | Example 4 |
|---|---|---|---|---|---|---|
| First agent (gel formulation) efficacy material | — | — | Iron chloride 0.5% | Iron chloride 0.5% Taurine 0.2% | Iron chloride 0.5% VitE 0.2% | Iron chloride 0.5% UDCA 0.2% |
| First agent (gel formulation) additive material | Glycerin 5% Silica 10% Povidone 10% Ethanol 10% Water to 100% | Glycerin 5% Silica 10% Povidone 10% Ethanol 10% Water to 100% | Glycerin 5% Silica 10% Povidone 10% Ethanol 10% Water to 100% | Glycerin 5% Silica 10% Povidone 10% Ethanol 10% Water to 100% | Glycerin 5% Silica 10% Povidone 10% Ethanol 10% Water to 100% | Glycerin 5% Silica 10% Povidone 10% Ethanol 10% Water to 100% |
| Second agent (patch) efficacy material | — | Hydrogen peroxide 3.0% | Hydrogen peroxide 3.0% | Hydrogen peroxide 3.0% | Hydrogen peroxide 3.0% | Hydrogen peroxide 3.0% |

Experimental Example 1. Whitening Effect Test-Brightness Variation

1) Test Method.

Comparative example 2 and examples 1 and 2 were each attached to a stained HAP disk and then removed after 1 hour, and variations relative to initial brightness were measured.

2) Test Results

Figure 1:
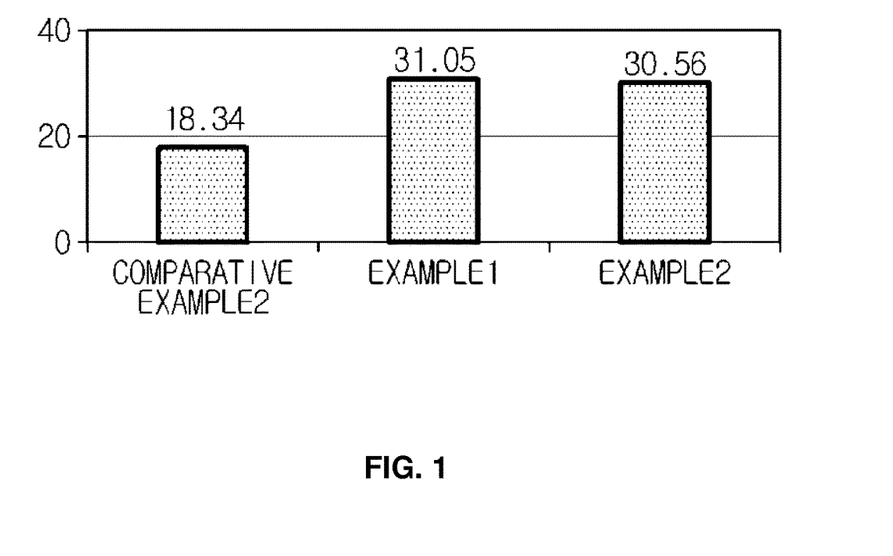
FIG. 1 is a graph showing variations in tooth brightness after the use of a kit for tooth whitening according to the present disclosure.

The results are shown in FIG. 1. As shown in FIG. 1, it could be seen that examples 1 and 2 showed an improvement in whitening effect by about 70% or more as compared to comparative example 2 using hydrogen peroxide alone.

Experimental Example 2. Patch Test Related to Irritation

1) Test Method 11 men having no skin disease on their arms were selected and comparative examples and examples were applied/attached in size of 2.5 cm×2.5 cm and kept for 1 hour. After removal in 1 hour, the remaining gel formulation was washed off with flowing water, and after 30 minutes, the degree of skin irritation was determined in accordance with the following judgment standard.

<Judgment Standard>

(CTFA/ICDRG Guideline, Textbook of Contact Dermatitis)

TABLE 2

| Reaction | Score | Symptoms and determination criteria |
|---|---|---|
| −+/−++++++ | 00.51.02.03.0 | No reaction Mild redness Moderate redness Serious redness involving swelling Serious redness involving blistering and swelling |

2) Test Results

Figure 2:
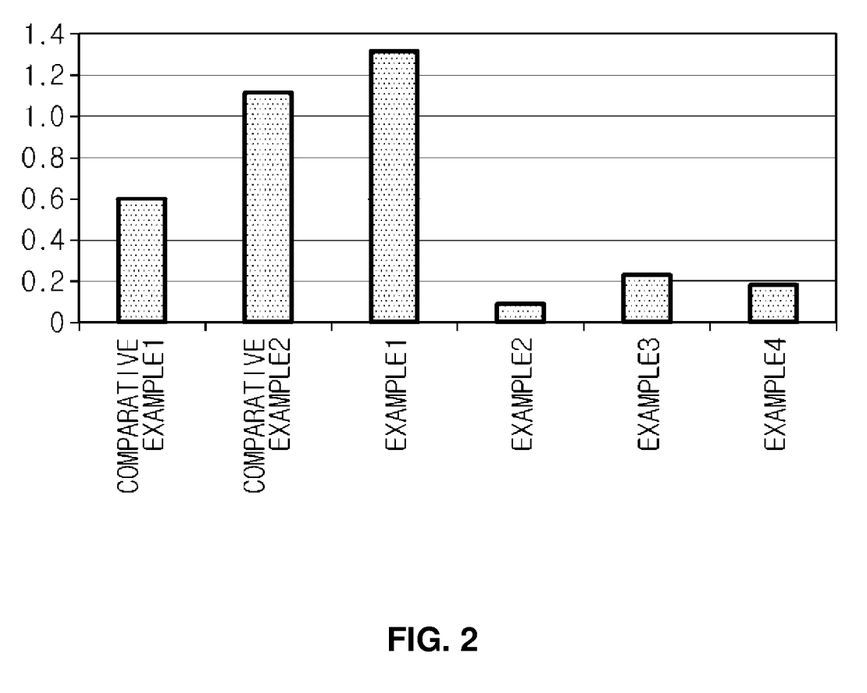
FIG. 2 is a graph showing the degree of skin irritation.

According to the results shown in FIG. 2, as a result of determining the degree of skin irritation, it could be seen that a skin irritation phenomenon was remarkably reduced in examples 2 through 4, compared to comparative examples 1 and 2. Particularly, it was found that example 2 containing taurine among the skin irritation mitigating ingredients showed a lowest degree of skin irritation.

Furthermore, it was demonstrated through experimentation that when the whitening ingredient activator is not used with the skin irritation mitigating ingredient, even stronger skin irritation might occur as compared to comparative examples 1 and 2.

Accordingly, when putting the results of experimental examples 1 and 2 together, the fact could be recognized that when the whitening ingredient activator is used with the skin irritation mitigating ingredient, an excellent tooth whitening effect could be obtained without causing irritation on the gum.

Experimental Example 3. Survey Evaluation Related to Irritation

After using comparative example 2 and examples 1 and 2, each subject was allowed to evaluate the degree of irritation on a 3-point scale according to the following evaluation criteria.

<Evaluation Criteria>
0: No irritation
1: Mild irritation
2: Certainly sensible irritation.
3: Stop using due to irritation According to the results shown in FIG. 3, it could be seen that in the case where iron chloride was used, the feeling of irritation was found more severe than the case where iron chloride was not used, but in the case where taurine was contained, the degree of feeling of skin irritation was significantly reduced.

Figure 3:
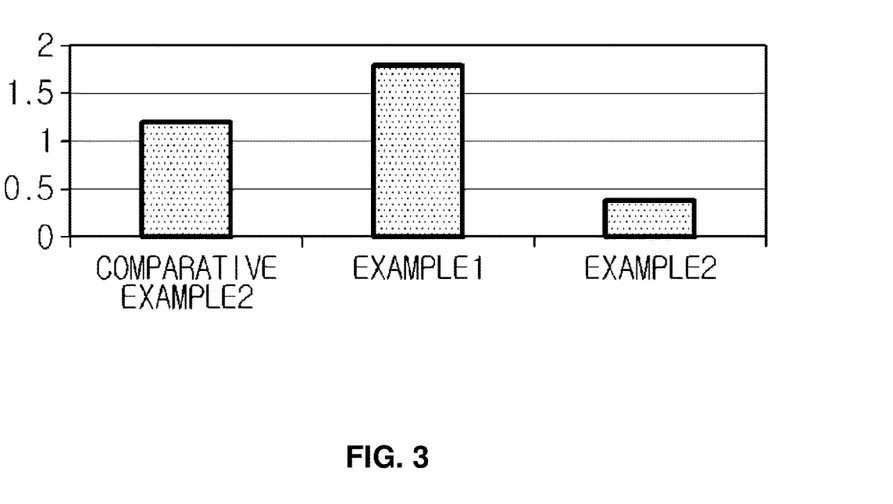
FIG. 3 is a graph showing survey evaluation results of the degree of irritation.

The survey evaluation results showed that skin irritation was alleviated by taurine similar to the patch test related to irritation of experimental example 2.

Example 5 and Comparative Examples 3-8

The kit for tooth whitening according to the present disclosure was produced according to the ingredient ratios as shown in the following Table 3, and the unit was indicated in wt %.

The gel formulation of the present disclosure was prepared by the following process.

After silica as an abrasive and iron chloride as an efficacy material were dissolved in a mixed solution of ethanol and water, povidone was added thereto, followed by stirring for 20 minutes.

The comparative example was prepared by the same method as example except the ingredients added.

After dissolving iron chloride in water, ethanol and silica were introduced, and when silica was found to be fully dispersed, povidone was introduced, followed by stirring for 20 minutes.

In addition, the patch for tooth whitening that is attached to the tooth included hydrogen peroxide as a whitening ingredient as shown below, and was produced in the same way as example 2 of U.S. Pat. No. 6,682,721.

TABLE 3

| | Comparative example 3 | Comparative example 4 | Comparative example 5 | Comparative example 6 | Comparative example 7 | Comparative example 8 | Example 5 |
|---|---|---|---|---|---|---|---|
| First agent (gel formulation) efficacy material | — | Ferrous gluconate 0.5% | Ferrous lactate 0.5% | Magnesium chloride 0.5% | Manganes chloride 0.5% | Iron sulfate 0.5% | Iron chloride 0.5% |
| First agent (gel formulation) additive material | Glycerin 5% Silica 10% Povidone 10% Ethanol 10% Water to 100% | Glycerin 5% Silica 10% Povidone 10% Ethanol 10% Water to 100% | Glycerin 5% Silica 10% Povidone 10% Ethanol 10% Water to 100% | Glycerin 5% Silica 10% Povidone 10% Ethanol 10% Water to 100% | Glycerin 5% Silica 10% Povidone 10% Ethanol 10% Water to 100% | Glycerin 5% Silica 10% Povidone 10% Ethanol 10% Water to 100% | Glycerin 5% Silica 10% Povidone 10% Ethanol 10% Water to 100% |
| Second agent (patch) efficacy material | Hydrogen peroxide 3.0% | Hydrogen peroxide 3.0% | Hydrogen peroxide 3.0% | Hydrogen peroxide 3.0% | Hydrogen peroxide 3.0% | Hydrogen peroxide 3.0% | Hydrogen peroxide 3.0% |

Experimental Example 4. Brightness Variation

1) Test Method

Comparative examples 3 through 8 and example 5 were each attached to a stained HAP disk and were removed after 1 hour, and variations relative to initial brightness were measured and were indicated as ΔL.

2) Test Results

Figure 4:
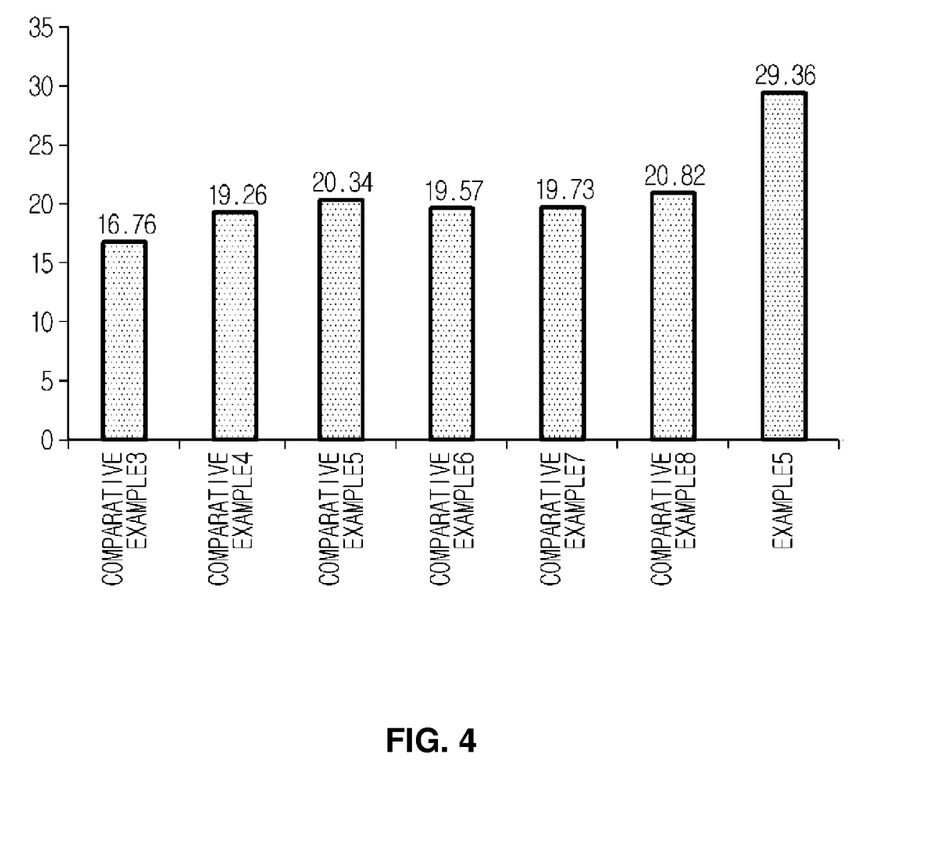
FIG. 4 is a graph showing measured variations relative to initial brightness of tooth samples.

It could be seen that the gel formulation containing the metal salt catalyst (comparative examples 3 through 8 and example 5) showed a higher whitening effect than comparative example 3 using the gel formulation with no efficacy material, and among them, the effect of example 5 using iron chloride was prominent. That is, it was demonstrated through experimentation that the composition containing iron chloride had a highest tooth whitening effect, and the results were shown in FIG. 4. The unit on the vertical axis of FIG. 4 was ΔL.

What is claimed is:

1. A method of whitening tooth, comprising:
    applying a first agent containing at least one selected from ursodeoxycholic acid, tauroursodeoxycholic acid, and taurine and a tooth whitening ingredient activator; and
    applying a second agent containing a tooth whitening ingredient and a peroxide stabilizer after applying the first agent,
    wherein the tooth whitening ingredient activator is $FeCl_3$, and
    wherein the first agent is in a gel formulation and the second agent is in a patch form.

2. The method according to claim 1, wherein the tooth whitening ingredient is at least one selected from hydrogen peroxide, carbamide peroxide, calcium peroxide, tetrasodium pyrophosphate peroxidate, sodium bicarbonate and a chloride-based bleaching agent.

3. The method according to claim 1, wherein the ursodeoxychlolic acid, tauroursodeoxycholic acid, and/or taurine is present in an amount of 0.001 wt % to 10 wt % per the total weight of the first agent.

* * * * *